(12) United States Patent
Galavotti

(10) Patent No.: US 11,617,818 B2
(45) Date of Patent: Apr. 4, 2023

(54) OXYGENATOR OF ORGANIC FLUIDS

(71) Applicant: QURA S.R.L., Mirandola (IT)

(72) Inventor: Daniele Galavotti, Mirandola (IT)

(73) Assignee: QURA S.R.L., Mirandola (IT)

( * ) Notice: Subject to any disclaimer, the term of this patent is extended or adjusted under 35 U.S.C. 154(b) by 759 days.

(21) Appl. No.: 16/496,977

(22) PCT Filed: Mar. 23, 2018

(86) PCT No.: PCT/IT2018/050052
§ 371 (c)(1),
(2) Date: Sep. 24, 2019

(87) PCT Pub. No.: WO2018/173092
PCT Pub. Date: Sep. 27, 2018

(65) Prior Publication Data
US 2020/0016312 A1 Jan. 16, 2020

(30) Foreign Application Priority Data
Mar. 24, 2017 (IT) .................. 102017000032687

(51) Int. Cl.
*A61M 1/16* (2006.01)
*A61M 1/26* (2006.01)
(Continued)

(52) U.S. Cl.
CPC .......... *A61M 1/1698* (2013.01); *A61M 1/262* (2014.02); *B01D 61/36* (2013.01);
(Continued)

(58) Field of Classification Search
CPC ................ A61M 1/1698; A61M 1/262; A61M 2205/366; A61M 2206/20; B01D 61/00;
(Continued)

(56) References Cited

U.S. PATENT DOCUMENTS

| 6,113,782 A | 9/2000 | Leonard |
| 2007/0249888 A1 | 10/2007 | Wu |
| 2015/0314059 A1 | 11/2015 | Federspiel |

FOREIGN PATENT DOCUMENTS

EP 1715279 10/2006

OTHER PUBLICATIONS

International Search Report filed in PCT/IT2018/050052 dated Jun. 19, 2018.

*Primary Examiner* — John Kim
(74) *Attorney, Agent, or Firm* — Rankin, Hill & Clark LLP

(57) ABSTRACT

The oxygenator of organic fluids comprises: a container body having a longitudinal axis; a first inlet opening for the oxygen and a second outlet opening for an exhaust gas obtained in the container body; a third inlet opening for an organic fluid to be oxygenated and a fourth outlet opening for oxygenated organic fluid obtained in the container body; an oxygenation chamber of the fluid to be oxygenated that is defined inside the container body; a distribution pre-chamber of the fluid to be oxygenated fitted between the third inlet opening and the oxygenation chamber; a mass of capillary fibers that are impermeable to liquids and porous to gasses, designed to be lapped by the organic fluid and arranged inside the oxygenation chamber according with a common parallel direction; dynamic distribution means supported in the distribution pre-chamber by support means.

11 Claims, 10 Drawing Sheets

(51) Int. Cl.
*B01D 69/08* (2006.01)
*B01D 61/36* (2006.01)

(52) U.S. Cl.
CPC ......... *B01D 61/362* (2013.01); *B01D 61/366* (2013.01); *B01D 69/08* (2013.01); *B01D 2311/2661* (2013.01); *B01D 2311/2688* (2013.01); *B01D 2313/04* (2013.01); *B01D 2313/20* (2013.01); *B01D 2313/26* (2013.01)

(58) Field of Classification Search
CPC .... B01D 61/36; B01D 61/362; B01D 61/366; B01D 63/02; B01D 69/08; B01D 2311/2661; B01D 2311/2688; B01D 2313/04; B01D 2313/20; B01D 2313/26; B01D 2313/08; B01D 2313/10
See application file for complete search history.

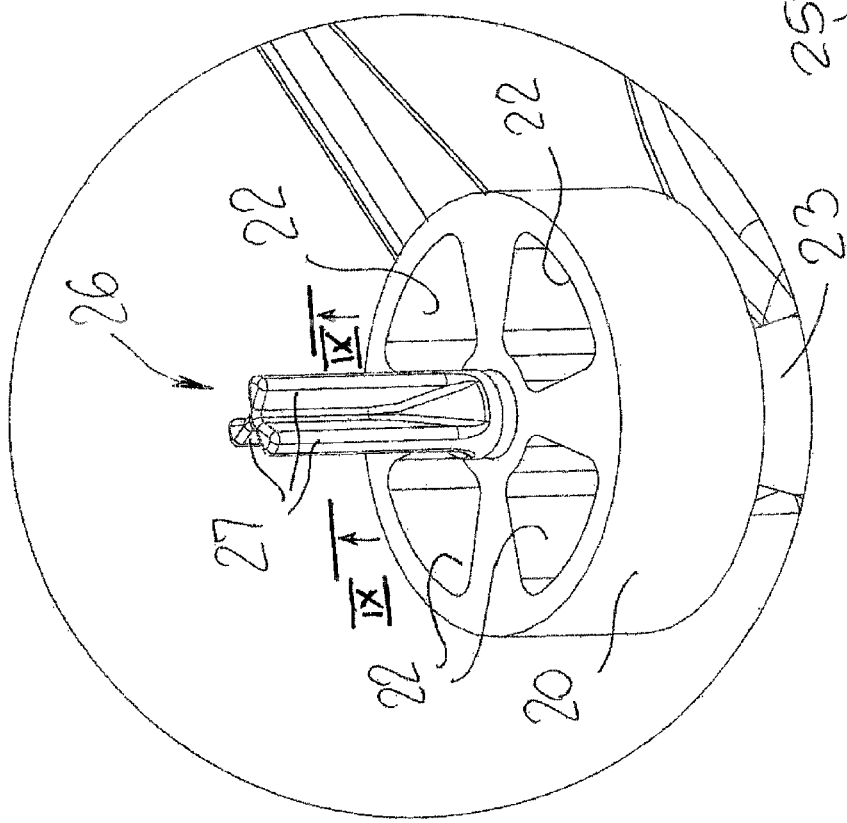
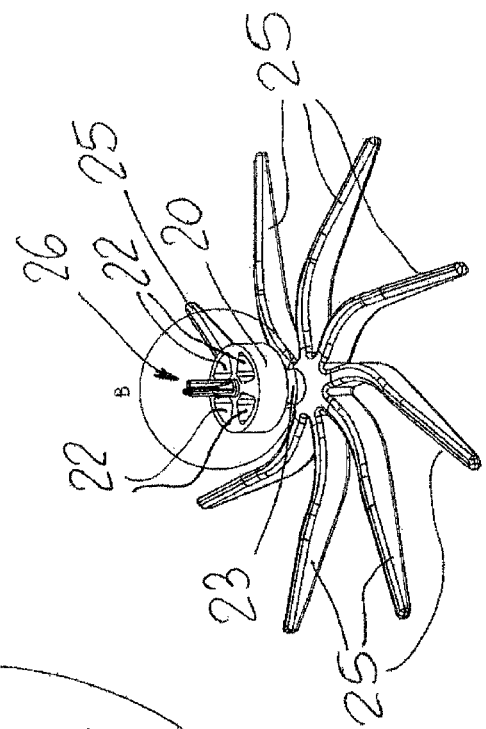
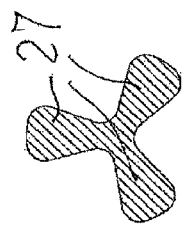
FIG. 7
FIG. 8
FIG. 9

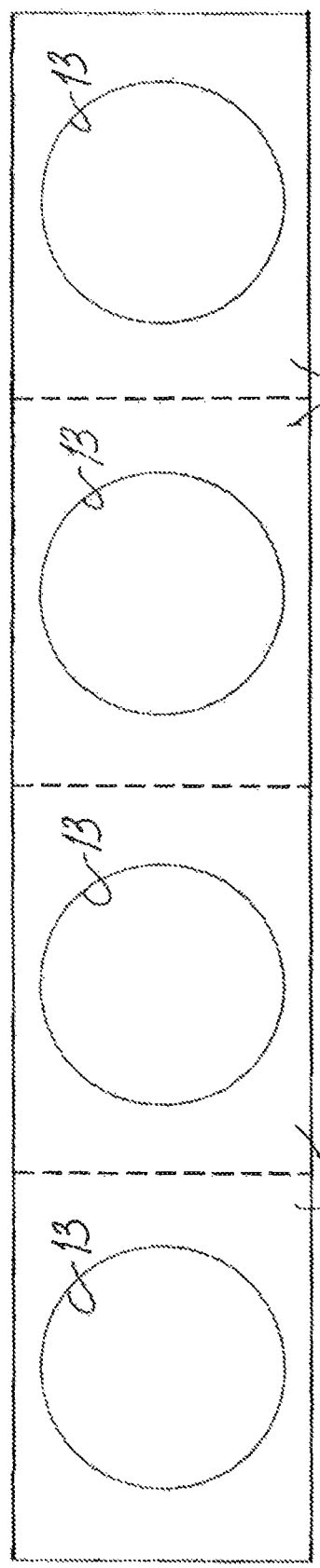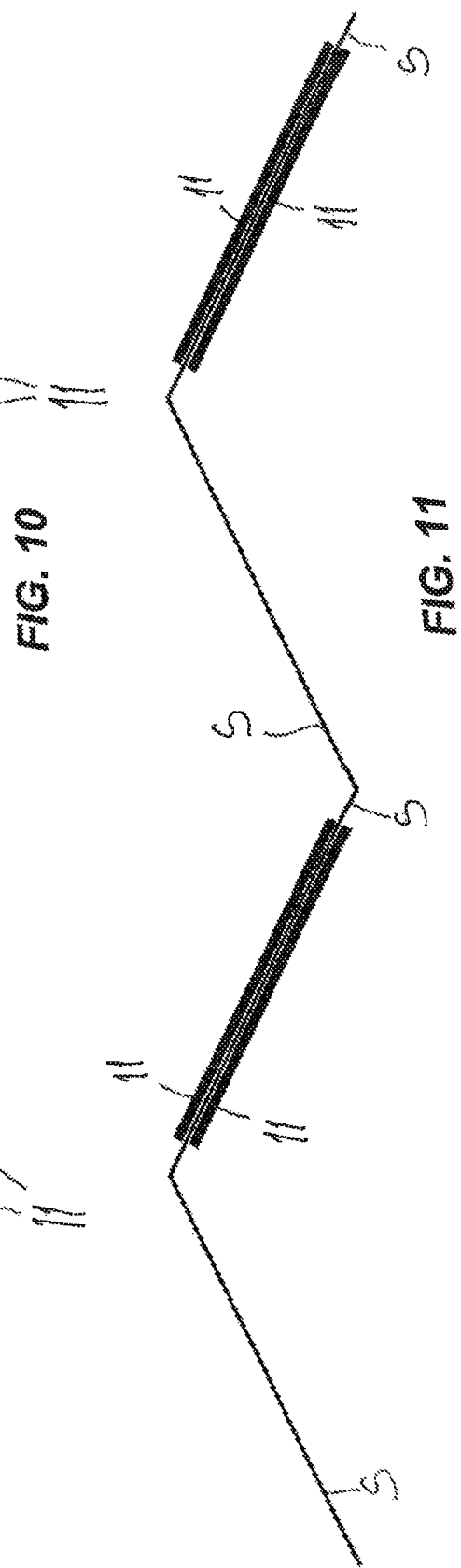

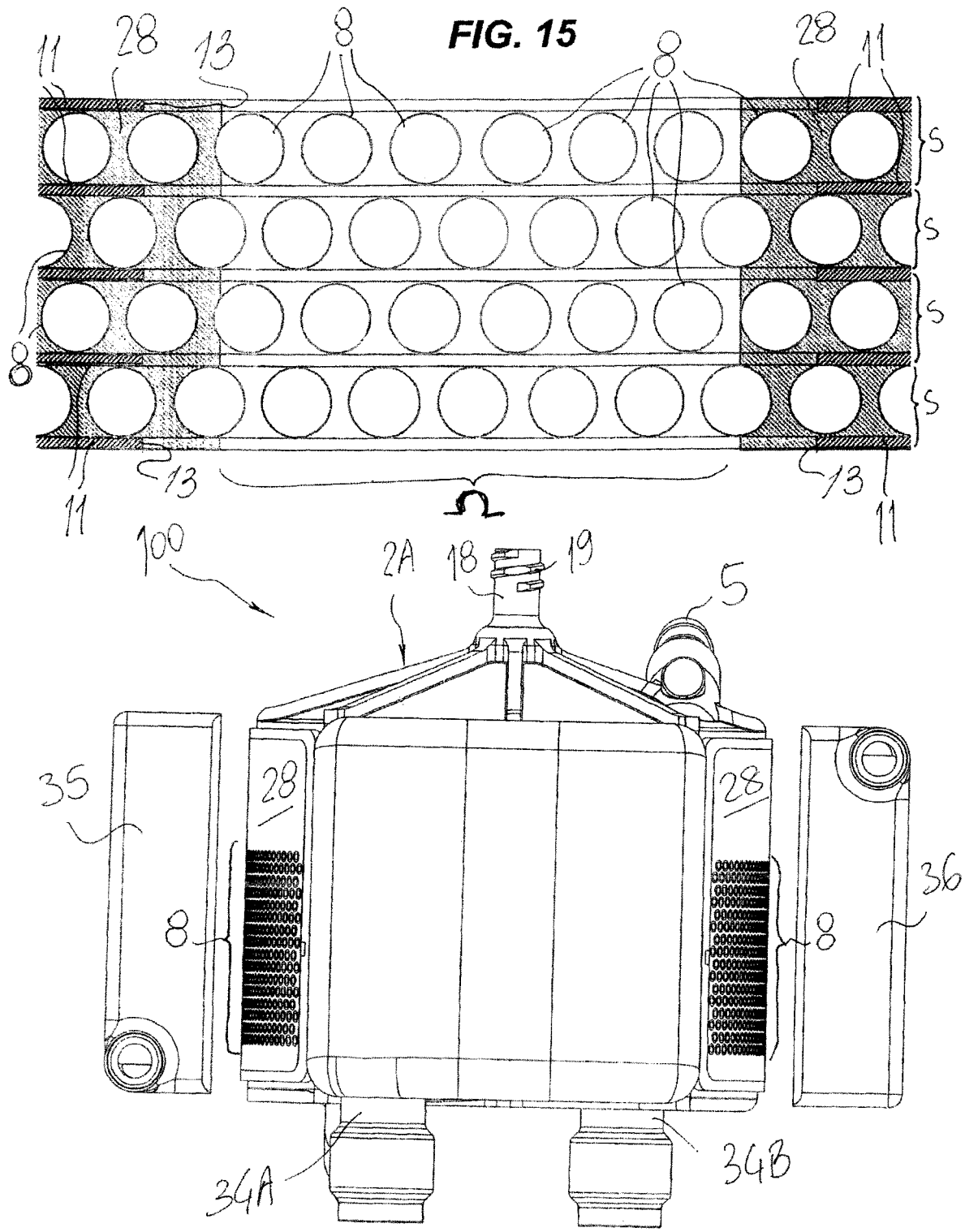

OXYGENATOR OF ORGANIC FLUIDS

FIELD OF APPLICATION

The invention concerns an oxygenator of organic fluids, which can be used in particular to oxygenate the blood flowing in an extracorporeal circuit, without forming zones where the flow of fluid slows and stagnates, which cause aggregates, clots and a significant reduction in oxygenation capacity.

STATE OF THE ART

Oxygenator devices have been known for a long time, hereafter referred to in brief as oxygenators, which are used to oxygenate an organic fluid, specifically blood, which flows in an extracorporeal circuit on which they are mounted and to which a patient subjected to oxygenation therapy is connected.

Typically, an oxygenator basically consists of a container which can have a cylindrical or parallelepiped shape, which defines inside itself a gas exchange chamber, or oxygenation chamber.

The oxygenator can also be equipped with another heat exchange chamber, in which the treated blood is heat-regulated before being re-introduced into the patient's circulatory system.

In the oxygenation chamber a mass of so-called hollow fibers is typically located, in practice segments of capillaries, which are parallel to each other and to the longitudinal axis of the oxygenator and which have open lumens at the respective opposite ends.

Each fiber is made of a material that is porous to gasses, but impermeable to liquids, so that it can only be passed through by a gas, in the specific case oxygen, during the passage of the blood flow that laps the external surface of the fibers in a direction orthogonal to the longitudinal axes of the latter.

The mass of fibers has all the open ends that end in respective chambers to accumulate the oxygen to be dispensed and to accumulate the carbon dioxide which is released from the blood during the gas exchange step.

The oxygen flows inside each fiber and is released into the flow of blood during the gas exchange, thus achieving the oxygenation process.

At the same time, the blood gives up carbon dioxide which permeates through the membrane thickness of the hollow fibers which channels the exhausted gas toward the collection compartment from which it is expelled toward the outside.

The mass of hollow fibers is in turn held back by so-called end "pottings", that is, by monolithic elements made of polyurethane-based materials which incorporate the ends, clamping them in the fixed position inside the oxygenation chamber.

Alternatively, in some oxygenators it is provided that the hollow fibers can also be held together with ligatures made with wires of micrometric thickness to further guarantee the correct geometrical reproducibility and dimensional stability of the hydraulic section which is obtained, for the benefit of the blood flow that normally flows outside them.

The mass of hollow fibers is typically made in the form of a skein which is rolled up on itself in a direction transverse to the fibers, so as to form a substantially cylindrical and elastically deformable body so as to be adapted to the size and shape of the oxygenation chamber.

In the container which forms the body of the oxygenator at least two openings are provided, for the oxygen to enter and the carbon dioxide given up in the gas exchange to exit, and at least two other openings for the entrance of the blood to be treated and the exit of the treated blood.

The person of skill understands that in the following description the term "treat" means "oxygenate", but also vice-versa.

A possible blood thermoregulation chamber is separated from the oxygenation chamber by means of pierced laminar elements and inside it provides to house a channel in which a thermoregulated fluid, typically water, is made to flow, which is introduced into the thermoregulation chamber through its own inlet opening and discharged through its own outlet opening.

The thermoregulation chamber is therefore located between the inlet opening of the blood to be oxygenated and the oxygenation chamber.

In a corresponding manner, downstream of the latter a collection chamber is provided in which the oxygenated blood accumulates before being re-introduced to the patient through the outlet opening of the oxygenated blood.

DISADVANTAGES OF THE STATE OF THE ART

The state of the art has some disadvantages.

A first disadvantage is that, despite the use in clinical practice of dosages of anticoagulant drugs, in the body of known oxygenators zones where the flow of blood to be oxygenated slows down are spontaneously created, which cause with time the formation of thrombi.

The thrombi, or parts of them, can in turn be transported to the patient, creating a risk for his/her safety, and also significantly reduce the useful section of for the passage of the blood, with consequent reduction in the effectiveness of the oxygenators.

A second disadvantage is that, in order to increase as much as possible the gas exchange surfaces between the hollow fibers and the blood which laps them, the oxygenation chambers of known oxygenators forcibly house skeins formed with numerous hollow fibers which are located in direct contact with each other and are therefore pressed against each other.

This forced pressing causes a crushing between the surfaces of the various capillary lumens passing through the hollow fibers in which the oxygen flows, causing, in this case as well, a considerable reduction of the nominal and useful gas exchange surfaces, directly in contact with the blood that flows around it.

This causes another reduction in the effectiveness of known oxygenators.

To avoid this negative characteristic, oxygenators are constructed which have sensitive sizes to allow to obtain an oxygenation chamber of sufficient volume to house inside it a large number of hollow fibers, but to the detriment of manageability, the overall bulk and quantities of material necessary to make these oxygenators.

A third disadvantage is that in known oxygenators, particularly in the vicinity of the inlet opening of the blood to be oxygenated, the latter is not distributed homogeneously over the entire surface of the skeins of hollow fibers contained in the oxygenation chamber.

This happens because, when entering the container body, the flow of blood tends to spontaneously follow a preferential path that makes its distribution on the exchange surfaces uneven.

This circumstance increases the tendency to accumulate blood in specific zones of the oxygenator and therefore the slowing down of the flow and the stagnation of the latter, with the consequent formation of clots and thrombi.

Another disadvantage of the prior art is that inside the hollow fibers, when it is provided that the ends of these are incorporated in the respective "pottings", an aqueous condensation tends to form, precisely in correspondence with the ends, caused by the difference in temperature between the median zones of the hollow fibers that are directly lapped by the blood that flows at body temperature of about 37° C., and the end zones that cannot be lapped by the blood because they are incorporated in the "pottings" which have varying thicknesses from zone to zone, depending on the chambers in which they are housed.

This condensation partly occupies the capillary lumens of the hollow fibers, forming an obstacle to the free flow inside them of the oxygen and reducing the overall efficiency of the gas exchange in known oxygenators.

PRESENTATION OF THE INVENTION

One purpose of the invention is to improve the state of the art.

Another purpose of the invention is to perfect an oxygenator of organic fluids which prevents the formation of blood clots and thrombi inside the body.

Another purpose of the invention is to provide an oxygenator of organic fluids which allows to optimize the useful surfaces both for gas exchange and also for the passage of the blood flows that lap the skeins of hollow fibers.

Another purpose of the invention is to provide an oxygenator of organic fluids which allows to distribute the blood uniformly at the entrance to the oxygenator, without causing slowing down of the blood flows and consequent stagnation thereof.

Another purpose of the invention is to provide an oxygenator of organic fluids which optimizes the ratio between the overall sizes and the oxygenation capacity.

Yet another purpose of the invention is to provide an oxygenator of organic fluids which considerably reduces the formation of condensation at the ends of the hollow fibers which form the gas exchange unit.

According to one aspect of the invention, an oxygenator of organic fluids is provided according to the characteristics of claim 1.

Further aspects of the invention are indicated in the dependent claims.

The invention allows to obtain the following advantages:
- to provide an oxygenator of organic fluids that has an advantageous ratio between overall sizes and oxygenation capacity;
- to provide an oxygenator of organic fluids that prevents the flow of organic fluids to be treated from slowing down and, consequently, the formation of accumulations and thrombi;
- to provide an oxygenator of organic fluids that prevents the crushing of the skeins of hollow fibers, keeping intact the useful passage sections and keeping all the surfaces of each single hollow fiber used perfectly pervious and usable, even in the case of high numbers of hollow fibers used in ratio to one unit of volume.

BRIEF DESCRIPTION OF THE DRAWINGS

Other characteristics and advantages of the present invention will become apparent from the detailed description of a preferential but non-restrictive embodiment of an oxygenator of organic fluids, shown by way of non-restrictive example with reference to the attached drawings wherein:

FIG. 7 is a view of a fan insulated by a distribution pre-chamber of the oxygenator according to the invention in which it is typically housed;

FIG. 8 is a view on a greatly enlarged scale of a portion of the fan in FIG. 7;

FIG. 9 is a view on a further enlarged scale of a detail of FIG. 8, taken from a trace section plane IX-IX of FIG. 8;

FIG. 10 is a plan view of a portion of the adhesive spacers used in combination with the skein of hollow fibers in FIG. 3;

FIG. 11 is a greatly enlarged schematic view of a portion of the skein of hollow fibers in FIG. 3 in a pre-prep configuration;

FIG. 14 is a schematic view of the oxygenator in FIG. 13, in an assembly step;

FIG. 15 is a schematic view of the structural organization of a portion of hollow fibers that are used in the oxygenator according to the invention.

DETAILED DESCRIPTION OF A PREFERRED EMBODIMENT

Figure 1:
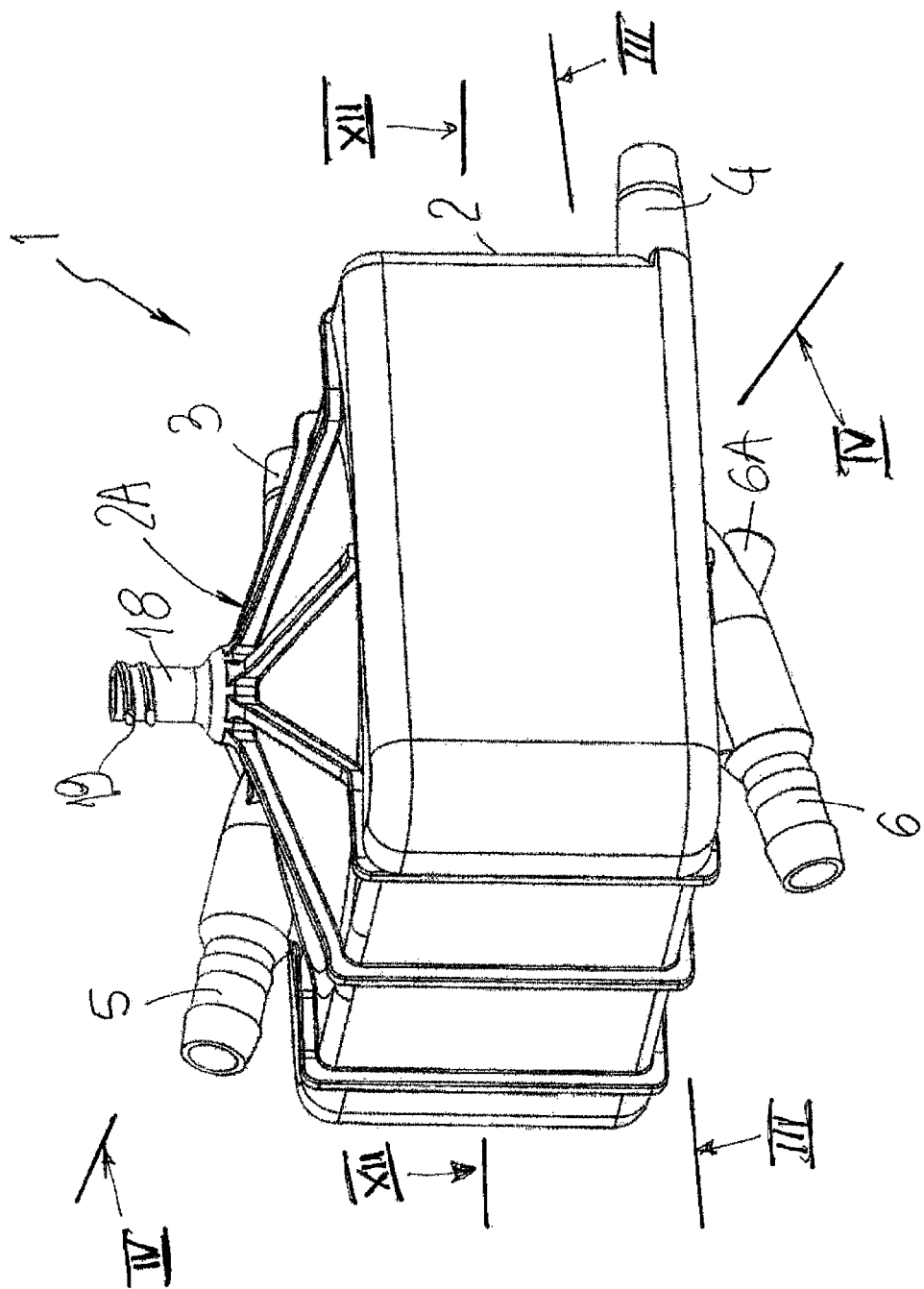
FIG. 1 is a perspective view of a first version of an oxygenator of organic fluids according to the invention.

With reference to the drawings cited, the number 1 indicates in its entirety an oxygenator of organic fluids, in a first possible embodiment, which has a container body 2 defining a longitudinal axis "A".

In the body 2 a first opening 3 is made from which the oxygen enters, and a second outlet opening 4 from which the exhausted oxygen exits, when, after the oxygenation process is complete, it is mixed with carbon dioxide released by the blood during the gas exchange, as will be described hereafter.

Also in the body 2 there is a third inlet opening 5 from which an organic fluid to be oxygenated enters, in this specific case blood, and a fourth outlet opening 6 from which the blood exits after being oxygenated.

Figure 2:
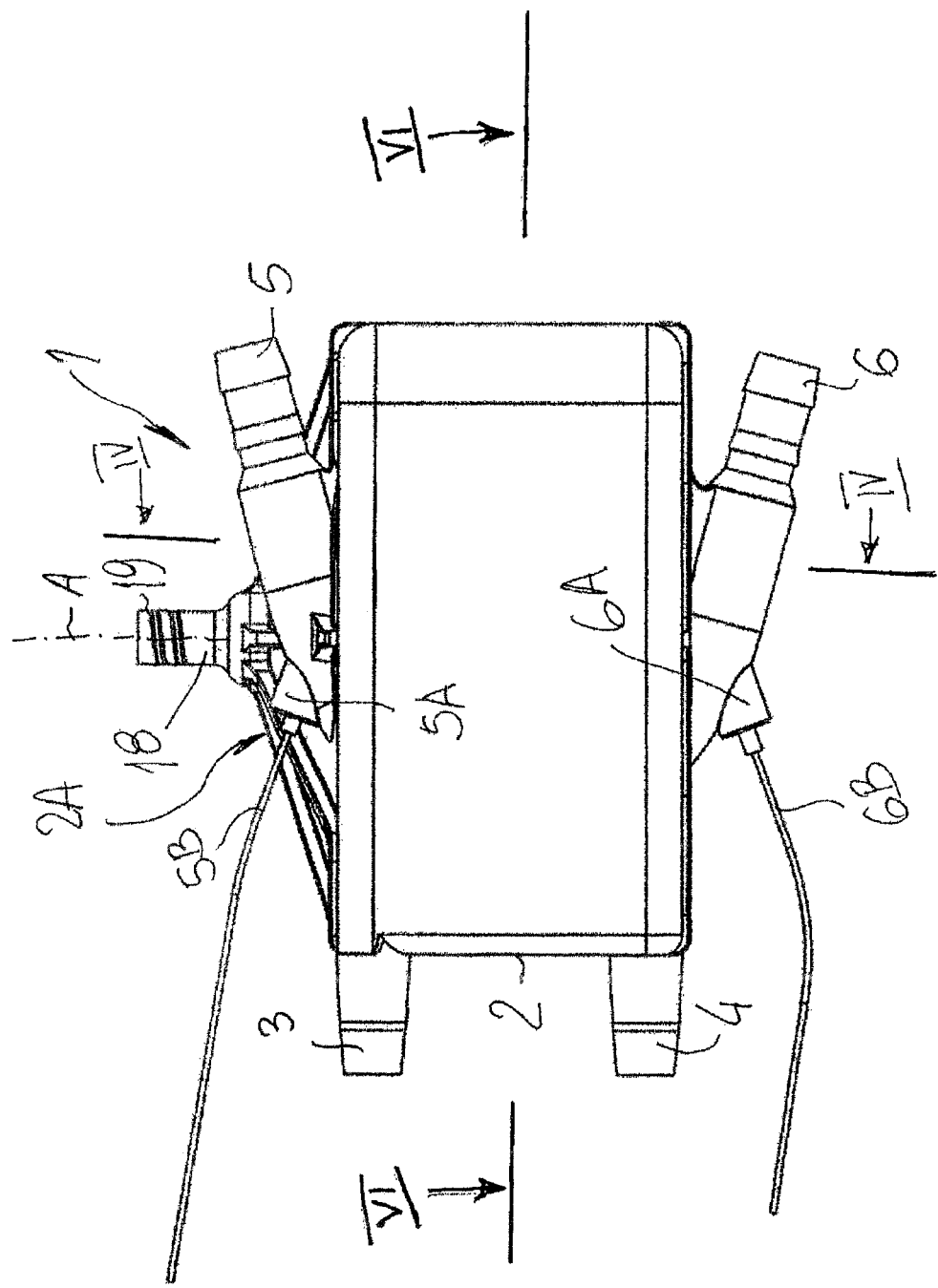
FIG. 2 is a lateral view of the oxygenator in FIG. 1, from a different view point.

With reference to FIG. 2, it should be noted that both in the third opening 5 and also in the fourth opening 6, precisely in the extensions of these toward the outside, two respective accesses 5A and 6A are made through which it is possible to introduce, in a sealed manner, or to fix, probes or sensors 5B and 6B to detect specific data of an organic fluid during its passage toward an oxygenation chamber 7, defined inside the body 2, and its outlet from the latter.

In the oxygenation chamber 7 a mass of elements are housed, suitable to perform the gas exchange and which consist of a multitude of hollow fibers 8 which are all joined together in parallel positions and which are associated in the form of a skein consisting of closely adjacent and substantially laminar layers.

Figure 4:
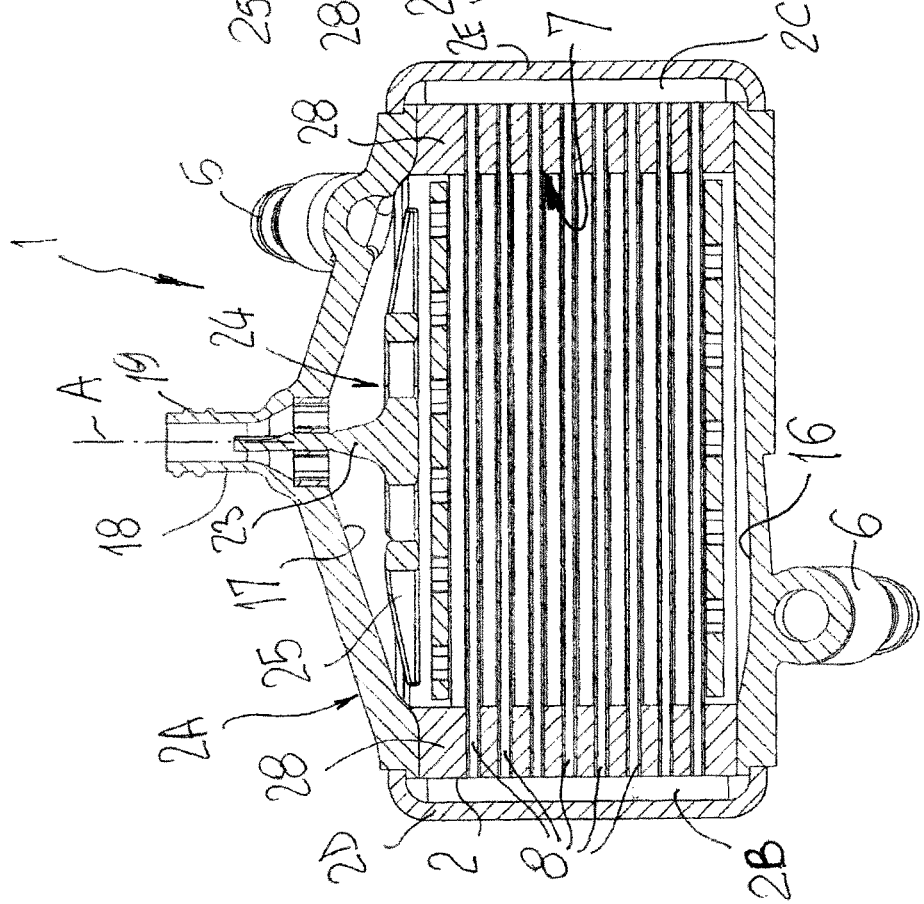
FIG. 4 is a schematic view in section of the oxygenator in FIG. 1, taken according to a trace plane Iv-Iv of FIG. 1.
Figure 5:
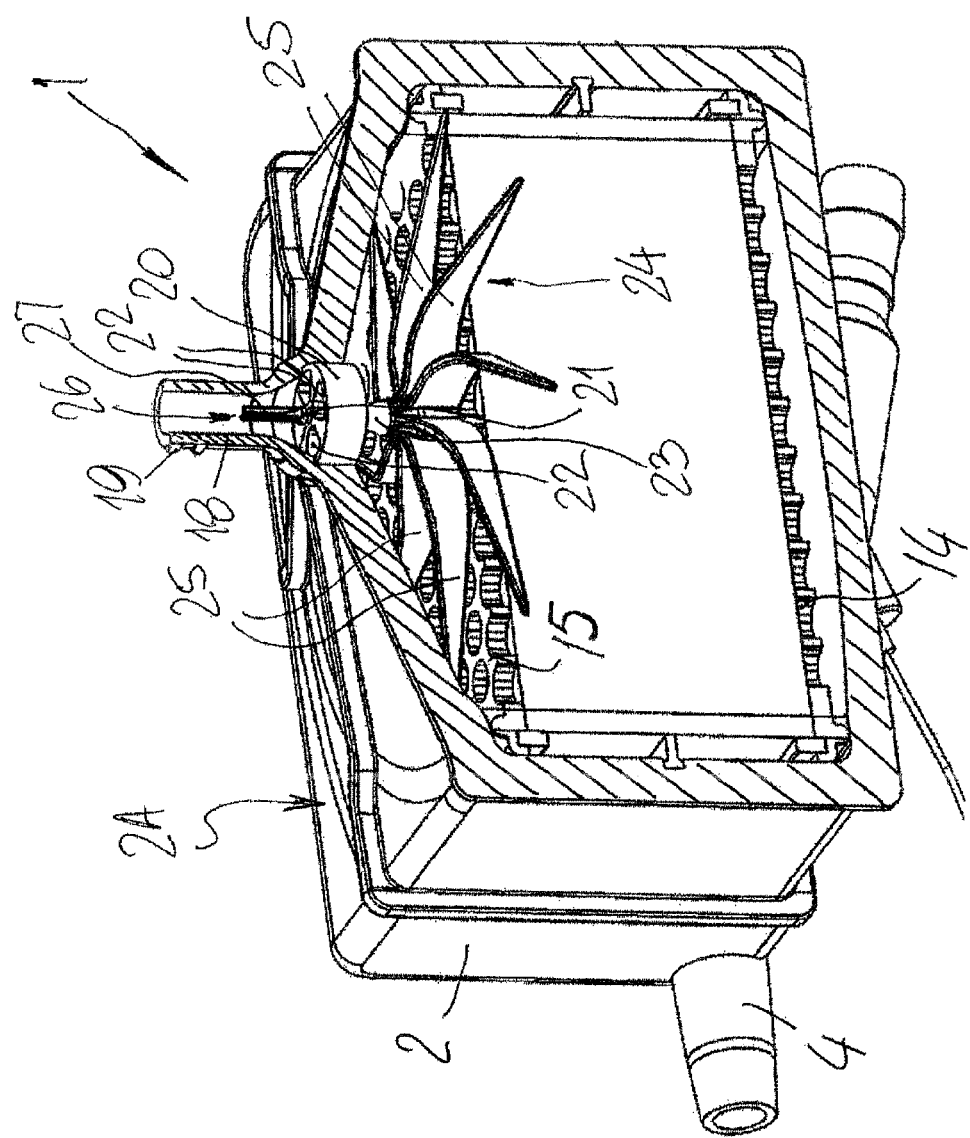
FIG. 5 is a partly sectioned schematic view of the oxygenator in FIG. 1.
Figure 6:
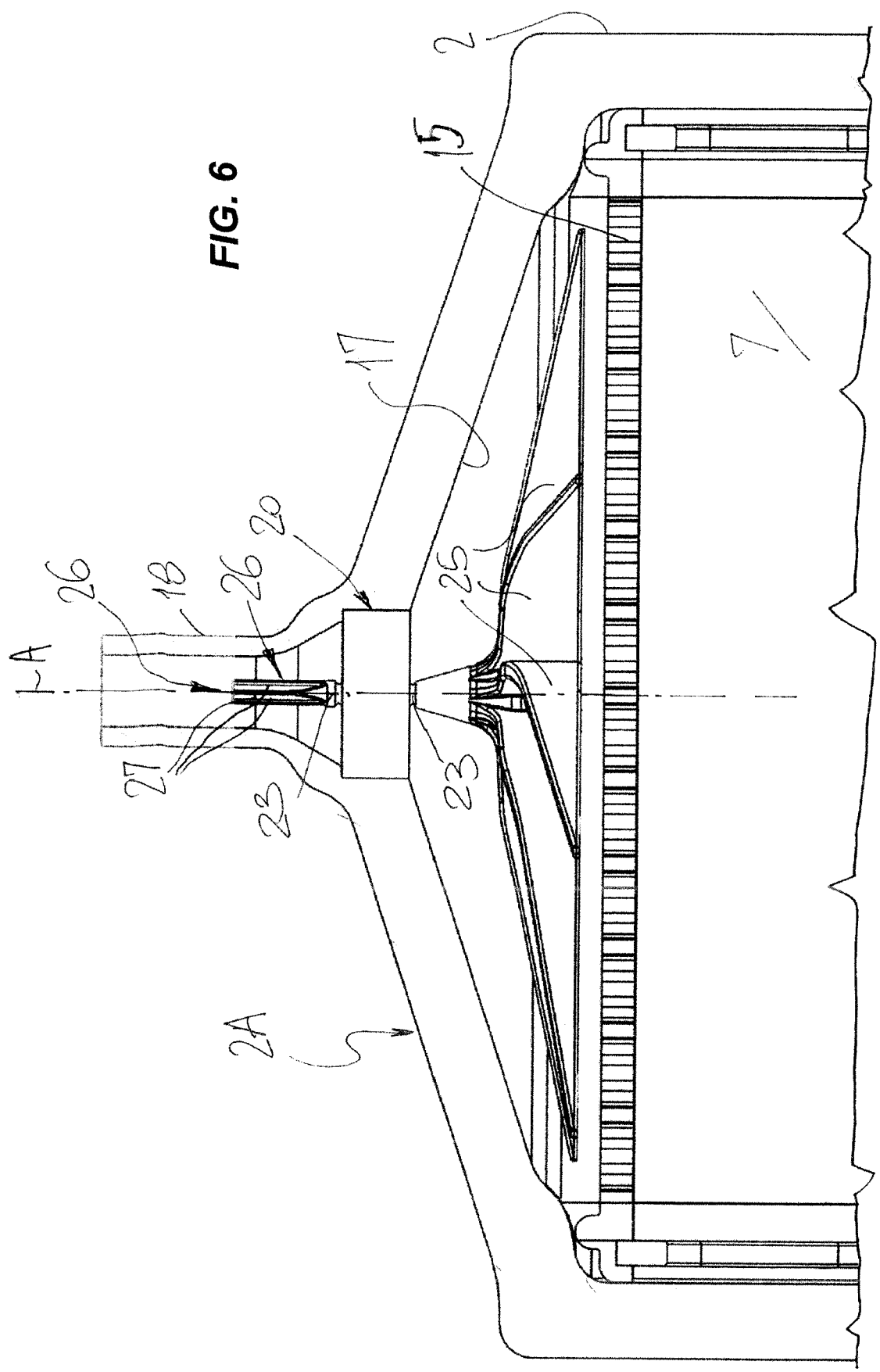
FIG. 6 is a schematic view, on an enlarged scale, of a zone of the oxygenator in FIG. 3 in which the entrance of the fluid to be oxygenated is provided.

As seen in FIG. 4, all the ends of the hollow fibers 8 end in corresponding chambers 2B, 2C which are defined between the body 2 and two corresponding lids 2D and 2E which are associated in a sealed manner with the body 2.

With reference to FIG. 11, this is a schematic view representing a portion of the skein of hollow fibers 8, arranged in an open configuration that precedes the packing into skeins and according to which the single loops are joined together according to common sides.

With reference to FIG. 11, the organization of the hollow fibers in a portion of skein and on a greatly enlarged scale can again be seen schematically.

As can be seen in FIGS. 10 and 11 and 15, spacer elements 11 are arranged between the layers "S" of the skein of hollow fibers 8, which have the function of keeping separate the hollow fibers 8 which form each layer "S".

In the preferred embodiment, the spacers 11 consist of sheets 12 of bi-adhesive material and each sheet 12 forms a through circular hole 13 at its center.

When all the holes of all the sheets 12 are superimposed on each other substantially concentrically, a central cylindrical through section "Ω" is formed, intended to be subsequently entirely incorporated in an element of plastic-polymeric material, indicated by 28 and typically known by the term "potting", defining a central cylindrical through section "Ω1" and coaxial to the previous "Ω" section through which the blood can flow during the gas exchange step, as will be described in detail hereafter.

As can be seen in FIGS. 3 to 6, the skein of hollow fibers 8 is contained between two pierced flat plates 14 and 15, which are fixed inside the oxygenation chamber 7 and which, with the inside of the body 2, respectively define a collection chamber 16 of the oxygenated blood, before it exits from the fourth opening 6, and a pre-chamber 17 which is defined between the third opening 5 and the oxygenation chamber 7.

As can be seen in the drawings, all the openings 3, 4, 5, 6 are equipped with respective mouths which have a standardized profile to allow to attach connectors for pipes that transport blood and oxygen and which extend toward the outside of the oxygenator.

In the body 2, specifically on the portion 2A considered the upper portion thereof, another fifth opening 18 is also provided which, like the others, is provided with a mouth in relief facing toward the outside, substantially cylindrical in shape, coaxial to the axis "A" and perimetrically equipped with a thread 19 to screw in a closing cap, not shown.

With reference to FIGS. 3 to 6, it can be seen that at the base of the fifth mouth 18, precisely where it connects to the pre-chamber 17, a bearing 20 is mounted which is coaxial with the axis "A" and which has a portion central 21 free to rotate.

Around the central portion 21 through openings 22 are provided which put the fifth opening 18 and the pre-chamber 17 in communication with each other.

The central portion 21 supports a central stem 23 which is coaxial with the axis "A" and which at the base forms dynamic distribution means 24 which are free to rotate inside the pre-chamber 17.

As can be seen in the drawings, the dynamic distribution means 24 are preferably made in the form of a fan having radial blades 25 which occupy a considerable part of the pre-chamber 17.

In detail, the stem 23 has an apical portion 26 which has a shaped profile which forms three radial fins 27, as can be seen in detail in FIGS. 8 and 9.

The radial fins 27 are suitable to keep the flows of blood in an agitated and moderately turbulent regime, in which there may be some undesired embolus of air which could accumulate at this point of the oxygenator 1, which is geometrically the highest inside the inlet chamber of the device, during use in the oxygenation step, to be expelled through the fifth opening 18, preventing the formation in the latter of accumulations and thrombi which, with time, would cause the occlusion thereof, rendering the oxygenator 1 unusable.

Figure 3:
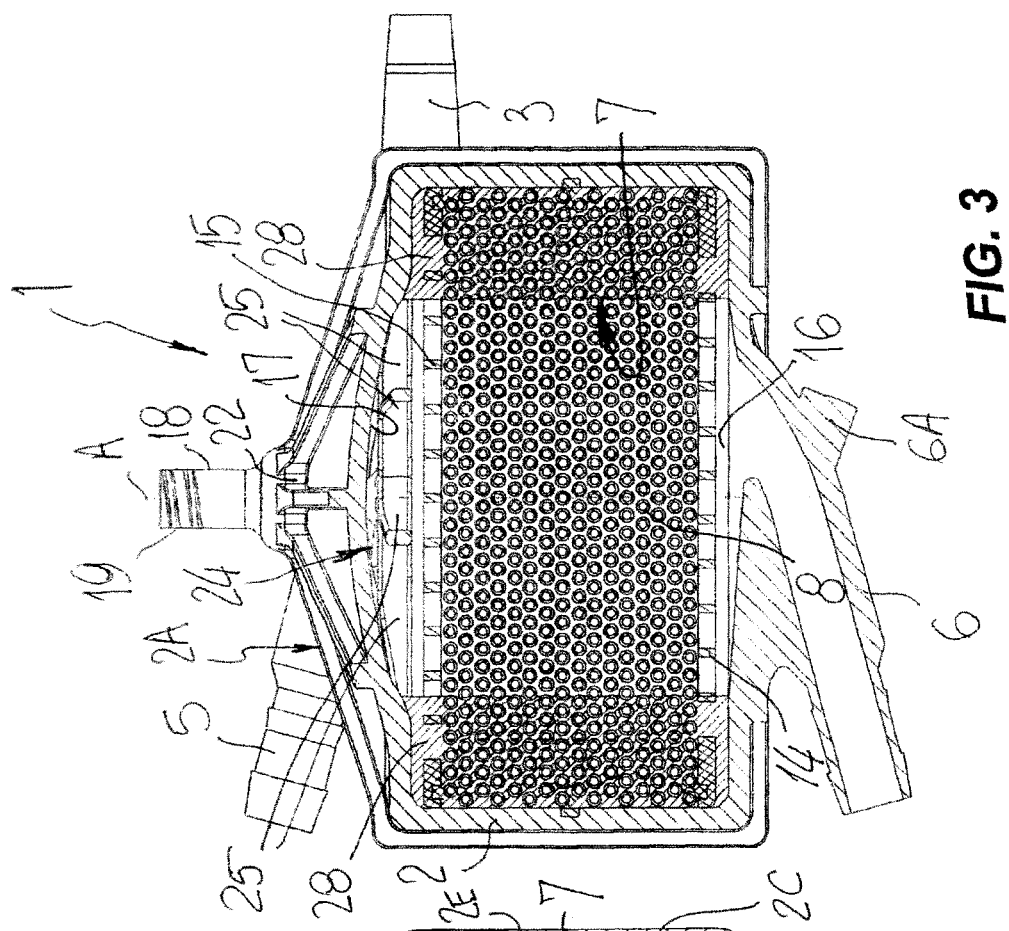
FIG. 3 is a schematic view in section of the oxygenator according to the invention, taken according to a trace plane of FIG. 1.
Figure 12:
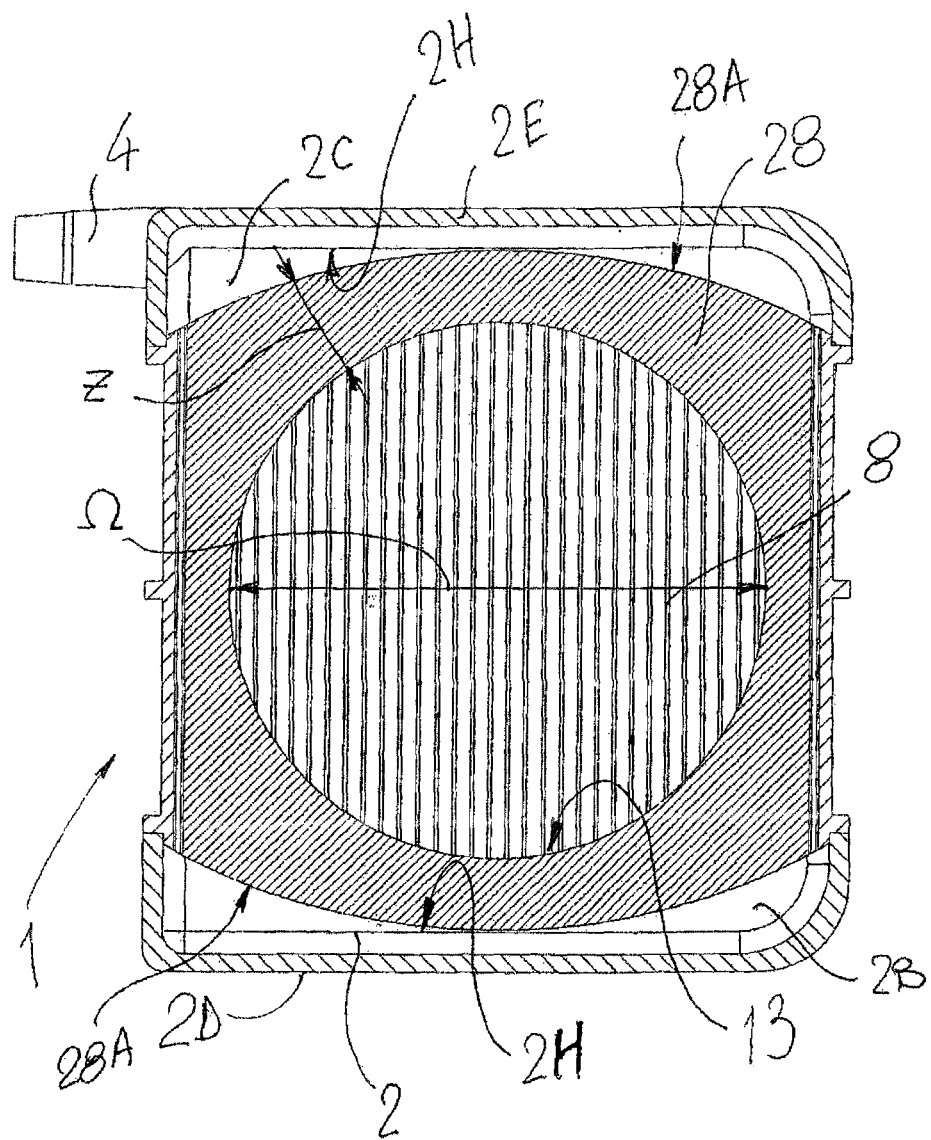
FIG. 12 is a cross section view of the oxygenator in FIG. 1 taken from a trace plane XII-XII.

With reference to FIGS. 3 and 4 and 12, it should be noted that the oxygenation chamber 7 contains in its internal perimeter the element of plastic-polymeric material, or "potting" mentioned above, indicated by 28, which incorporates inside it both the ends of the skein of hollow fibers 8 and also the perimeter zone of the layers "S" and the corresponding spacers 11 inserted between them, which determine the cylindrical through section "Ω" entirely incorporated by the "potting", which is cylindrical in shape, which, leaving the through section "Ω1" free, also cylindrical and formed by the coaxial alignment of the holes 13 made in the latter, and also the end portions of the two pierced plates 14 and 15, holding the whole in a single fixed block.

Figure 13:
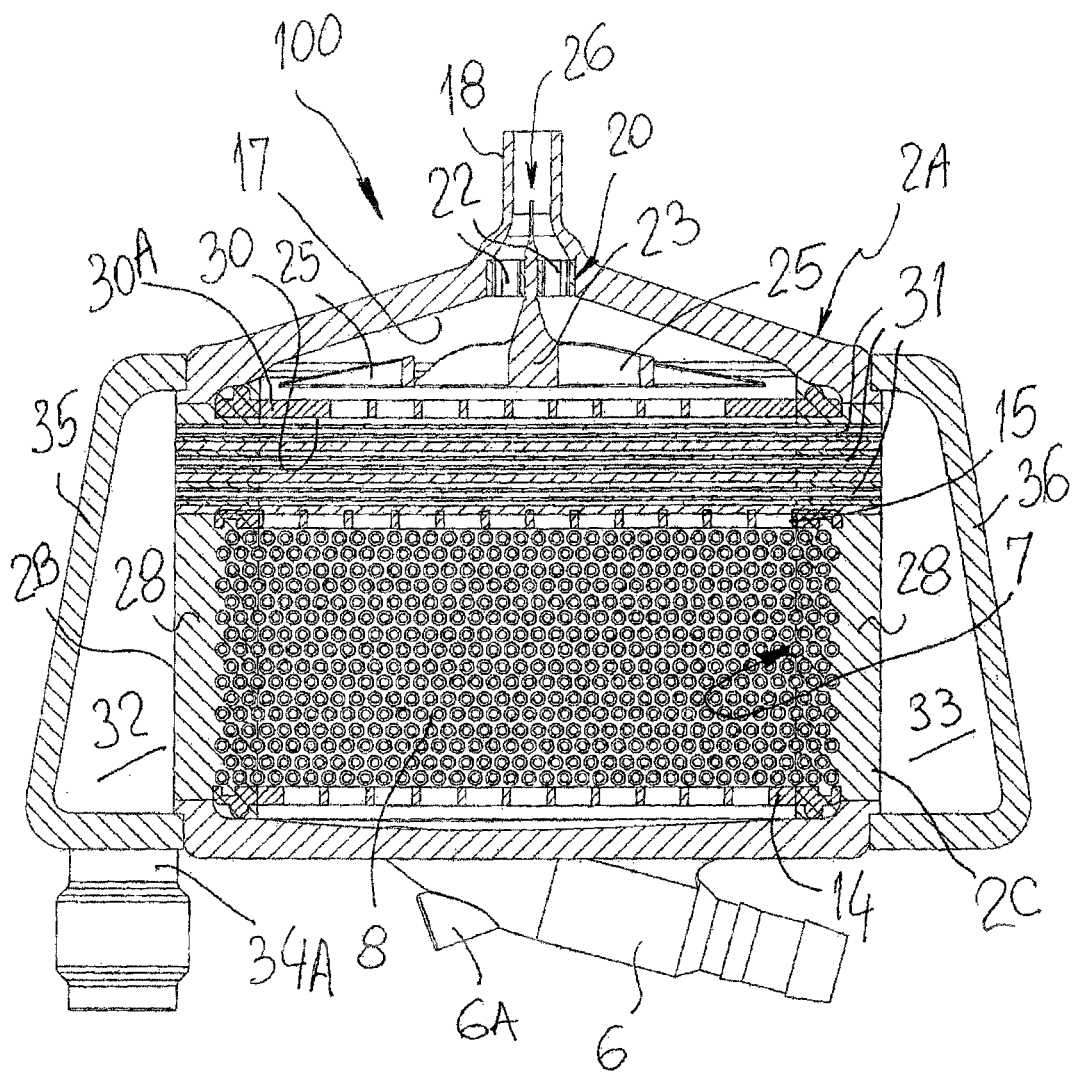
FIG. 13 is a section view of the oxygenator according to the invention, in a second implementation version.

With reference to FIG. 13, a second implementation version of the oxygenator according to the invention can be seen.

In this drawing, the common elements have been indicated with the same numerical references as in the previous version.

In detail, the oxygenator, indicated by 100, again comprises a body 2 which is equipped with inlet and outlet openings for a gas, in this specific case oxygen, however not visible in the drawing, and with openings for the inlet and outlet of an organic fluid which is to be oxygenated, in this specific case blood: of these last openings, only the fourth outlet 6 of the oxygenated blood is visible.

Also in this second version, the body 2 defines inside it an oxygenation chamber 7 (or also gas exchange chamber in general), in which a mass of hollow fibers 8 organized in the form of a skein formed by laminar layers "S" of hollow fibers 8 parallel to each other is arranged.

As in the previously described version, spacers are interposed between the layers "S", which in FIG. 8 are not perceptible to the observer due to the reduced scale.

The mass of hollow fibers 8 is interposed between two laminar plates 14 and 15 which are pierced to allow the blood to pass through them.

The substantial difference between this second version of the oxygenator 100 compared with the first version is that in this second version, between the distribution pre-chamber 17 and the oxygenation chamber 7, another thermoregulation chamber 30 is obtained in which capillaries 31 are housed, open and parallel to each other.

More in detail, the thermoregulation chamber 30 is defined between the laminar plate 15 and another laminar plate 30A, parallel to the laminar plate 15, which is mounted in correspondence with the distribution pre-chamber 17.

The ends of the capillaries 31 end in corresponding lateral chambers 32 and 33 which are obtained in the body 2 and which are provided with openings 34A and 34B, also in this case provided with corresponding extension mouths, which communicate with the outside of the body 2.

Precisely, the two chambers 32 and 33 are obtained by applying two respective lids 35 and 36 in a sealed manner on external and opposite faces 2B and 2C of the body 2.

Typically, from one of the openings 34 a thermoregulated fluid can enter, that is, heated or cooled with respect to the body temperature of a patient, while the thermoregulated fluid can exit from the other opening 34.

The two lateral chambers 32 and 33 are in communication with the thermo-regulation chamber 30 to allow the thermo-regulated fluid to pass inside the capillaries 31, so that the organic fluid to be subjected to oxygenation is heated or cooled as required, during its passage through the oxygenator 100.

With reference to FIG. 12, it should be noted that the perimeter profile of the "potting" 28, indicated by 28A, is substantially rounded and does not follow the rectilinear profiles of the internal walls 2H of the two chambers 2B, 2C defined between the lids 2D, 2E and the body 2.

This characteristic allows to reduce the thickness "Z" of the "potting" 28, especially in the zones in which it incorporates the ends of the hollow fibers 8.

This reduction in thickness allows to significantly reduce the formation of condensation inside the ends of the hollow fibers 8, since the difference in temperature is reduced between the zones in which the blood flows passing through the useful section "$\Omega 1$", lapping the median portions of the hollow fibers 8 and the temperature of the ends of the latter.

DESCRIPTION OF FUNCTIONING

The oxygenator of organic fluids according to the first implementation version functions as follows: the organic fluid to be oxygenated, in this specific case blood, is thrust by a pump that, through an extracorporeal circuit, takes it from a patient, directly or through the interposition of a venous blood collection tank, sends it to the oxygenator 1 and, from this, recirculates it to the patient.

The blood, in detail, enters through the third opening 5, flows into and occupies the pre-chamber 17 in which the dynamic distribution means 24, in practice a fan 24 which rotates and has radial blades 25, thrust by the flow of the blood itself, and is evenly distributed on the surface of the pierced plate 15.

The blood passes through the pierced plate 15 and penetrates inside the oxygenation chamber 7, lapping the external surfaces of the hollow fibers 8 grouped together in a skein.

The blood passes in the cylindrical useful section "$\Omega 1$" which is defined between the layers "S" which form the skein of hollow fibers 8.

At the same time, an oxygen flow is introduced into the oxygenator 1 through the first opening 3, accumulating in the chamber 2B in which concurrent ends of the hollow fibers 8 end.

The oxygen then flows inside the hollow fibers 8 during the lapping of the latter by part of the blood.

The porous nature of the hollow fibers 8 to gasses allows to obtain the gas exchange between oxygen and the blood which, in turn, gives up carbon dioxide which is collected inside the hollow fibers 8.

The oxygenated blood then collects in the collection chamber 16 and from here is thrust toward the patient through the fourth outlet opening 6.

The carbon dioxide present in the hollow fibers 8 after the gas exchange is collected in the chamber 2C and from there is sent toward the outside through the second outlet opening 4.

When the blood to be oxygenated enters the oxygenator 1, occupying the pre-chamber 17, it releases possible air bubbles which are expelled through the fifth opening 18, after removal of the closing lid with which it is normally provided.

The rotation of the fan 24 and of the shaft 23 keep the lumen of the fifth opening 18 constantly pervious by means of the dynamic action of the fins 27 which are formed at the end of the shaft 23, preventing harmful and undesirable accumulations and clots of blood inside the lumen of the fifth opening 18.

When the blood flows inside the oxygenation chamber 7, it flows, as we said before, inside the useful passage section "$\Omega 1$" which has the overall shape of a pervious cylinder.

The circular sections of the holes 13A which, aligned and substantially coaxial with each other, form the useful section "$\Omega 1$", prevent the formation of angles and/or recesses which, being present in known oxygenators, create preferential paths of the blood flows and, as a consequence, distinct zones in which the speeds of the blood flow may be different from each other, in particular they create zones in which accumulations and clots can arise due to the strong slowing down of the flow speeds.

In the alternative implementation version, the oxygenator 100, in the gas exchange step, functions in the same way as described above for the first version.

The substantive difference is that in the second version, the blood, during its passage inside the oxygenator 100, can also be thermoregulated.

Thermoregulation, which can be performed both to increase the temperature and also to decrease it, is performed by introducing a previously thermoregulated liquid, typically water, with known thermoregulation means, through the opening 34A, first by accumulating it in the lateral chamber 32, then by making it flow inside the capillaries 31 which are housed in the thermoregulation chamber 30, and then collecting it in the lateral chamber 33, before making it exit through the opening 34B.

In the preferred embodiment, the capillaries 31 of the thermoregulation chamber 30 are preferably oriented at a right angle to the hollow fibers 8 of the oxygenation chamber 7.

In this way, the blood, flowing from the pre-chamber 17 toward the oxygenation chamber 7, passes through the other laminar plate 30A, laps the capillaries 31 perimetrically, heating up or cooling down due to contact until it reaches a desired temperature.

The presence of the spacers 11 between the layers "S" of hollow fibers 8 which form each of these allows to prevent crushing in a transverse direction of each hollow fiber 8, keeping the axial lumen pervious and, in short, leaving the entire external circumferential surface thereof completely free, allowing the passage of oxygen and carbon dioxide without any physical obstacle during the gas exchange process.

It is also to be stressed that the particular rounded shape of the perimeter walls of the "potting" 28 considerably attenuates the formation of condensation inside the lumens of the hollow fibers 8, thus maintaining them pervious for the passage of oxygen.

In practice it has been found that the invention achieves the intended purposes.

The invention as conceived is susceptible to modifications and variants, all of which come within the inventive concept.

Furthermore, all the details can be replaced by other technically equivalent elements.

In its practical implementation, the materials used as well as the shapes and sizes may be any whatsoever, according to requirements, without departing from the field of protection defined by the following claims.

The invention claimed is:

1. An oxygenator of organic fluids comprising:
    a container body having a longitudinal axis;
    a first inlet opening for the oxygen and a second outlet opening for an exhaust gas obtained in said container body;
    a third inlet opening for an organic fluid to be oxygenated and a fourth outlet opening for oxygenated organic fluid obtained in said container body;
    an oxygenation chamber of said organic fluid to be oxygenated that is defined inside said container body;
    a distribution pre-chamber of said organic fluid to be oxygenated fitted between third inlet opening and said oxygenation chamber;
    a mass of capillary fibers that are impermeable to liquids and porous to gases, designed to be lapped by said organic fluid and clamped by clamping means inside said oxygenation chamber according with a common parallel direction, said fibers being arranged in a package comprising loops of contiguous layers of fibers, transversally positioned with respect to said longitudinal axis and contained between at least two containing pierced plates which are housed reciprocally parallel in said oxygenation chamber; and
    dynamic distribution means supported in said distribution pre-chamber by support means,
    wherein spacing members comprising sheets of bi-adhesive material are interposed between said contiguous layers, said spacing members being fully encapsulated in a plastic-polymeric element;
    wherein between said contiguous layers at least a central cylindrical usable section is perpendicularly defined, coaxial to said longitudinal axis, designed to be passed through by said organic fluid.

2. The oxygenator as claimed in claim 1, wherein said dynamic distribution means comprise at least a fan that is supported freely rotatable by said support means inside said pre-chamber, said at least one fan including a central stem and a plurality of radial blades.

3. The oxygenator as claimed in claim 2, wherein said central stem is coaxial to said longitudinal axis.

4. The oxygenator as claimed in claim 2, wherein said support means comprise at least one bearing that is fixed in an opposing end of a mouth, coaxially to said longitudinal axis, and which supports said central stem, at least one end of said central stem extending in said mouth with a shaker portion.

5. The oxygenator as claimed in claim 1, wherein said distribution pre-chamber includes a fifth discharge opening outside said oxygenator.

6. The oxygenator as claimed in claim 5, wherein said fifth opening is obtained coaxially to said longitudinal axis and shapes a mouth having an extended end toward an outside of said container body and an opposing end emerging in said distribution pre-chamber, said support means being housed in said opposing end.

7. The oxygenator as claimed in claim 6, wherein said support means comprise at least one bearing that is fixed in said opposing end of said mouth, coaxially to said longitudinal axis, and which supports a central stem, at least one end of said central stem extending in said mouth with a shaker portion.

8. The oxygenator as claimed in claim 1, wherein said clamping means comprise at least one plastic-polymeric element, having two opposing walls encapsulating corresponding homologous opposing ends of said fibers and housed in said oxygenation chamber.

9. The oxygenator as claimed in claim 8, wherein said opposing walls have a rounded profile.

10. The oxygenator as claimed in claim 8, wherein between said at least one plastic-polymeric element and said container body at least an oxygen amassing chamber wherein first homologous ends of said fibers end and an exhaust gas amassing chamber wherein second ends of said fibers end are defined.

11. The oxygenator as claimed in claim 1, wherein between said distribution pre-chamber and said oxygenation chamber a thermoregulation chamber of said organic fluid to be oxygenated is defined, wherein a thermoregulated fluid flows in a flowing circuit arranged in said thermoregulation chamber.

* * * * *